US009470645B2

(12) United States Patent
Klein et al.

(10) Patent No.: US 9,470,645 B2
(45) Date of Patent: Oct. 18, 2016

(54) SALT-BASED METHOD TO MONITOR AND LOG THE TIMES A DATA CENTER AIR GOES ABOVE A PREDEFINED LIMIT

(71) Applicant: International Business Machines Corporation, Armonk, NY (US)

(72) Inventors: Levente Klein, Tuckhoe, NY (US); Prabjit Singh, Poughkeepsie, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/821,261

(22) Filed: Aug. 7, 2015

(65) Prior Publication Data

US 2015/0346128 A1 Dec. 3, 2015

Related U.S. Application Data

(63) Continuation of application No. 14/248,572, filed on Apr. 9, 2014.

(51) Int. Cl.
| | |
|---|---|
| *G01N 7/00* | (2006.01) |
| *G01N 27/04* | (2006.01) |
| *B01D 53/30* | (2006.01) |
| *B01D 53/02* | (2006.01) |
| *G01N 27/12* | (2006.01) |

(52) U.S. Cl.
CPC ............ *G01N 27/048* (2013.01); *B01D 53/02* (2013.01); *B01D 53/30* (2013.01); *G01N 27/121* (2013.01); *B01D 2257/80* (2013.01)

(58) Field of Classification Search
CPC .................................................. G01N 27/048
USPC ................ 73/335.02, 335.05, 335.06, 23.21, 73/29.01, 29.05
See application file for complete search history.

(56) References Cited

U.S. PATENT DOCUMENTS

| | | | |
|---|---|---|---|
| 3,715,702 A | 2/1973 | Nicholas | |
| 4,041,437 A * | 8/1977 | Matsuura | G01N 27/12 252/194 |
| 4,473,813 A | 9/1984 | Kinjo et al. | |
| 4,642,601 A | 2/1987 | Sugawara et al. | |
| 4,752,855 A | 6/1988 | Fedter et al. | |
| 5,136,274 A * | 8/1992 | Shimomura | G01N 27/121 338/35 |
| 5,533,393 A * | 7/1996 | Bonne | G01N 27/121 324/663 |

(Continued)

FOREIGN PATENT DOCUMENTS

| | | |
|---|---|---|
| CN | 102291273 A | 12/2011 |
| JP | 2002-214180 | 7/2002 |
| JP | 2008-061575 | * 3/2008 |

OTHER PUBLICATIONS

IBM, "List of IBM Patents or Patent Applications Treated as Related (Appendix P)," May 26, 2016, p. 1-2.

*Primary Examiner* — Hezron E Williams
*Assistant Examiner* — Hoang Nguyen
(74) *Attorney, Agent, or Firm* — Robert C. Bunker

(57) ABSTRACT

A salt-based method to monitor and log the time periods a data center air's relative humidity goes above a predefined limit. The choice of the salt is such that its deliquescent relative humidity is equal to the desired limit, so that above the desired limit, the salt gets wet and therefore electrically conductive. An alarm can then give notice that relative humidity levels are above acceptable levels so that remedial action may be taken before problems such as electronic malfunction develop.

5 Claims, 4 Drawing Sheets

(56) References Cited

U.S. PATENT DOCUMENTS

| | | | |
|---|---|---|---|
| 5,608,374 A * | 3/1997 | Ikejiri | G01N 27/121 252/963 |
| 5,861,758 A * | 1/1999 | Berberich | B60S 1/0818 318/483 |
| 6,568,265 B2 * | 5/2003 | Shibue | G01N 27/121 427/103 |
| 6,742,387 B2 | 6/2004 | Hamamoto et al. | |
| 7,461,539 B2 | 12/2008 | Galun et al. | |
| 7,552,635 B2 * | 6/2009 | Chang | G01N 27/048 73/335.05 |
| 8,869,596 B2 * | 10/2014 | Hagl | A61B 5/441 73/29.02 |
| 2004/0031339 A1 * | 2/2004 | Swanson | G01N 25/56 73/865.9 |
| 2012/0144906 A1 * | 6/2012 | Knyrim | G01N 31/222 73/73 |
| 2015/0293046 A1 | 10/2015 | Klein et al. | |

* cited by examiner

SALT-BASED METHOD TO MONITOR AND LOG THE TIMES A DATA CENTER AIR GOES ABOVE A PREDEFINED LIMIT

BACKGROUND

Electronic equipment exposed to high levels of relative humidity in surrounding air may often times corrode. Early mitigation of high relative humidity conditions may avoid such problems.

SUMMARY

In an embodiment, an apparatus to monitor the relative humidity of air going above a predefined value is provided. The apparatus includes: metallic, inter-digitated comb patterns printed on a medium having spacing in between the patterns wherein a saturated liquid solution containing salt is dried upon the medium, the salt having a deliquescent relative humidity, wherein the dried salt absorbs moisture and becomes ionically conductive when exposed to relative humidity levels exceeding the salt's deliquescent relative humidity. Also included is a power supply and a high resistance resistor connected to the inter-digitated comb pattern in series and forming an electrical circuit; and a microprocessor connected across the high resistance resistor which monitors changes in resistance of the circuit that result from the salt becoming ionically conductive thereby indicating an incident of relative humidity of the air exceeding a predefined value based on the salt's deliquescent relative humidity.

In another embodiment, an apparatus to monitor the relative humidity of air going above a predefined value is provided.

The apparatus includes: a sand blasted printed circuit board comprising
metallic, inter-digitated comb patterns printed on a medium having spacing in between the patterns wherein a saturated liquid solution containing salt is dried upon the medium, the salt having a deliquescent relative humidity, wherein the dried salt absorbs moisture and becomes ionically conductive when exposed to relative humidity levels exceeding the salt's deliquescent relative humidity. Also included is a power supply and a high resistance resistor connected to the inter-digitated comb pattern in series forming an electrical circuit; and a microprocessor connected across the high resistance resistor which monitors changes in resistance of the circuit that result from the salt becoming ionically conductive thereby indicating an incident of relative humidity of the air exceeding a predefined value based on the salt's deliquescent relative humidity.

In another embodiment, a method to monitor the relative humidity of air exceeding a predefined value is provided. The method includes:
providing metallic inter-digitated comb patterns printed on a medium having spacing in between the patterns; coating the patterns and medium with a liquid solution containing salt, the salt having a deliquescent relative humidity;
allowing the solution to dry; connecting, in series, a power supply, a high resistance resistor and a microprocessor to the comb pattern thereby creating an electrical circuit; connecting at least one of a data logger and an alarm circuit to the microprocessor; monitoring, by the microprocessor, the resistance of the circuit as a current passes through the circuit; and triggering the alarm circuit in response to the current exceeding a threshold value.

DETAILED DESCRIPTION

The industry wide recommended relative humidity limit below which electronic hardware is designed to operate reliably is 60%. Relative humidity in data centers above this limit can cause electronic components to malfunction, potentially resulting in computing disruption and loss of data.

The present invention relates to a salt-based device and a circuit to monitor and log the time periods a data center air's relative humidity goes above a predefined limit so that action may be taken before problems such as electronic malfunction develop. Current techniques of measuring the relative humidity are based on sensor technology that has an accuracy of ±2% or even more. With the ever increasing use of outside air for cooling IT equipment, there is a need to monitor the relative humidity of the air forced into the data center to cool the IT equipment. The need to monitor the air for relative humidity is even more relevant on rainy, damp or very humid days when the combination of mechanical cooling combined with outside air cooling can lead to condensation and enhanced corrosion. Dew point measurement may provide an alternative for data center moisture level monitoring, but the dew point is calculated from relative humidity and temperature data. Both temperature and relative humidity have a measurement error that is propagated along the dew point calculation which may lead to inaccurate measurements.

Deliquescent relative humidity is the relative humidity above which salt absorbs water and thus gets wet and ionically conductive. The deliquescent relative humidity is solely determined by the chemical properties of the salt used for monitoring. As long as the salt remains pure, its deliquescent relative humidity will remain unchanged.

In an embodiment, a very precise relative humidity data logger device utilizing salt and based on sodium nitrite chemistry is shown. The deliquescent relative humidity of the salt chosen to build the device should be near or equal to the desired relative humidity limit. The salt is dissolved preferably in distilled water to limit impurities to maintain consistent deliquescent relative humidity.

Sodium nitrite is a good choice for building the device because its deliquescent relative humidity is 62% which is quite close to the desired relative humidity limit of 60%. The device is reliable and virtually fail-safe device and can raise an alarm when the relative humidity rises above 62%, which is the deliquescent relative humidity of sodium nitrite. Devices based on other salts will raise the alarm at other relative humidity levels above the deliquescent relative humidities of the salts. For example, if sodium chloride is chosen, the alarm will go off when the relative humidity rises above the 75% deliquescent relative humidity of sodium chloride. The device can also store the history of the alarm situations and maintain a records to track times and occurrences of excessive relative humidity in the air.

Figure 1:
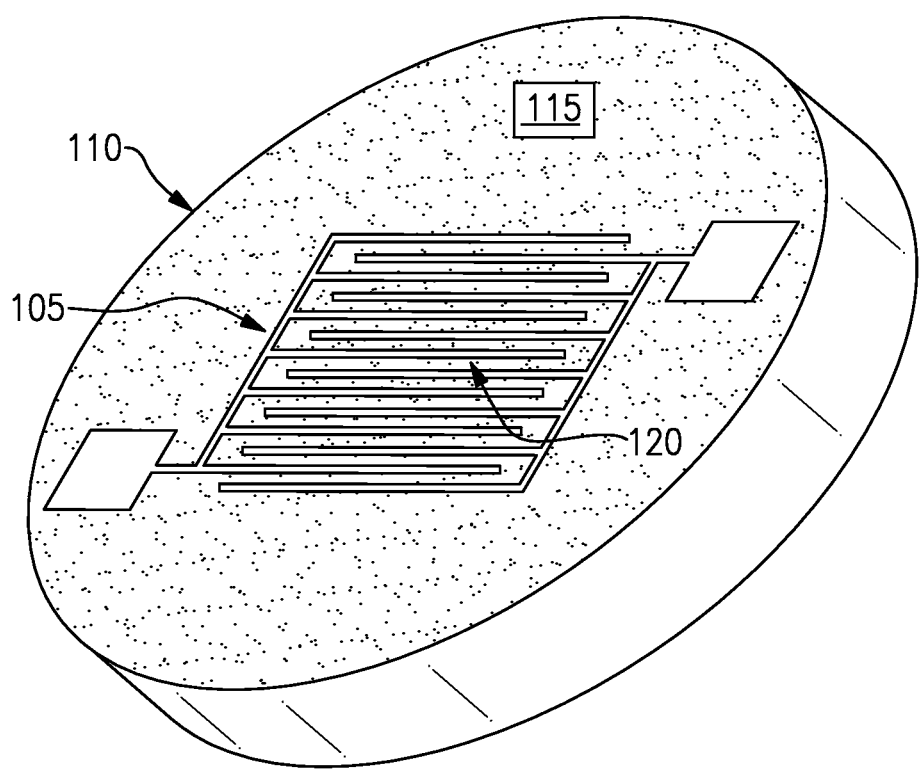
FIG. 1 depicts a platinum inter-digitated comb coupon printed on a 2-mm thick quartz frit disk. The pores in the frit contain sodium nitrite salt.

With regards to FIG. 1, an inter-digitated comb pattern 105, preferably made of platinum, a very corrosion resistant metal, is printed on a quartz frit disk 110 whose pores contain sodium nitrite salt particles 115. Quartz frit consists of fused quartz particles with interconnected pores. Quartz frit is commercially available, generally, to filter liquids in chemistry laboratories. The salt particles cannot fall off the disk because they are trapped in the interconnected pores in the frit disc.

The quartz frit disk is soaked in sodium nitrite solution so that the solution penetrates the pores in the quartz frit. The solution is then dried. The concentration of the solution may be saturated. Preferably, the solution is saturated with salt by adding more salt than the solution can dissolve. For example, for a given salt, there is a fixed amount of salt the water can dissolve. Each salt has a solubility limit; i.e. sodium chloride has a solubility limit of 35 g in 100 ml of water and sodium nitrite has a solubility limit of 81 g in 100 ml of water. As an example, 90 gm of sodium nitrite is added to 100 mg of distilled water. Of the nitrite added, 81 g will dissolve. The rest will settle to the bottom of the beaker. The top liquid can be decanted to be used as the salt solution to soak the quartz frit or the circuit board. The undisclosed solid sodium nitrite may be discarded.

The comb patterns may be separated by about 0.5 mm spacing 120. The comb patterns may consist of platinum plating. Platinum is preferred because of its corrosion resistance to most salts and environments. Other metals with similar properties such as gold or palladium may also be used.

Another implementation of the sensor may use the inter-digitated comb pattern printed on other substrates besides the quartz frit disk such as on printed circuit boards that have been sand blasted to make the board surface rough enough to retain the salt particles bridging the combs. The pits on the printed circuit board between the combs may be loaded with salt particles by drying the saturated salt solution applied to the board. The circuit board surface may be roughened up for better adherence to the salt solution. The inter-digitated comb pattern may be made of other metals besides platinum or gold.

Figure 2:
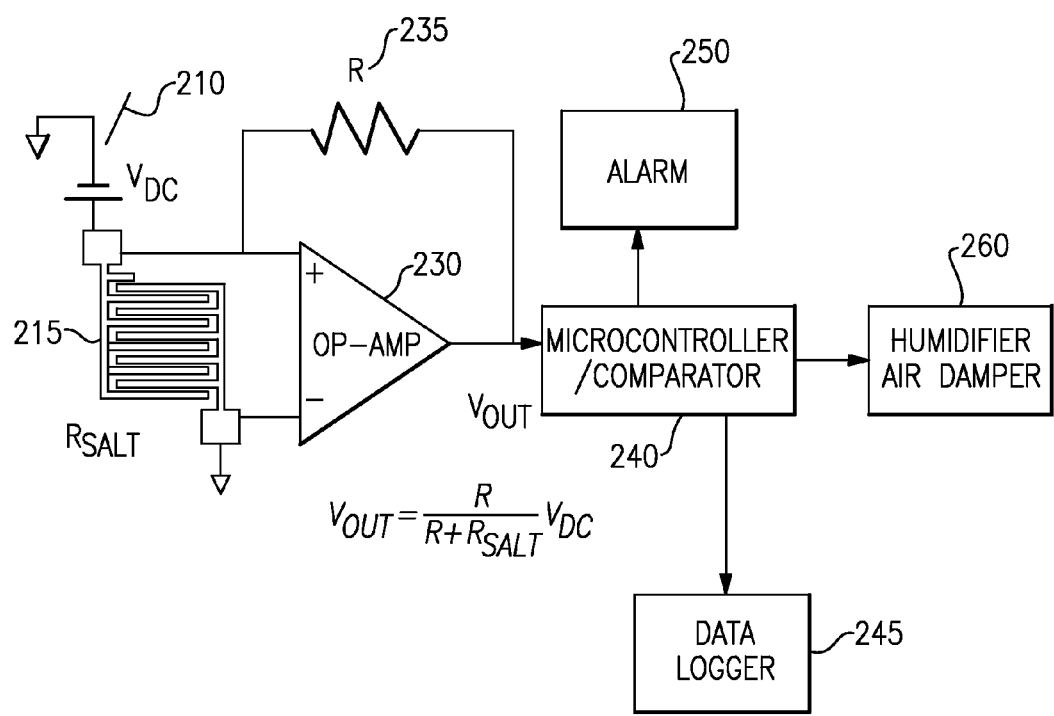
FIG. 2 describes the circuit used to detect when the relative humidity rises above a predetermined level.

FIG. 2 depicts a sample implementation of the comb patterns in an electrical circuit, with the comb pattern sensor printed on the same circuit board as the electrical circuit that is used to monitor high relative humidity events. A small constant voltage from power source 210 of about 1 V is applied across the inter-digitated patterns while the current flowing between the two comb electrodes is measured continuously. The power source may be a battery. An operational amplifier 230 will convert the current into voltage. The resistance R 235 across the operational amplifier can be of the order of 1 MOhm. Under low relative humidity conditions, the conductivity between the two inter-digitated patterns is very low (resistance between the comb electrodes can be larger than 100 MOhm), and the measured current would be less than 10 nA. The voltage from the circuit is monitored continuously by a microcontroller 240 that would have a voltage threshold programmed into it. Resistance and voltage levels are monitored by microcontroller 240.

As the relative humidity increases, the sodium nitrite salt will remain relatively dry, with high electrical resistance, until the air relative humidity approaches 62%. Above 62% relative humidity, the salt will absorb moisture and get wet and therefore become electrically conductive; the microcontroller 240 will detect the rise of current between the inter-digitated comb patterns. A rise of current from 10 nA to >1 mA is expected, as the relative humidity crosses the 62% threshold. If the leakage current goes above 1 mA, the microcontroller will cause alarm 250 to trigger and the data will be recorded in data logger 245. The alarm indicates an incident of relative humidity in the air exceeding a pre-defined value.

If the relative humidity in the data center goes above 62%, the salt gets wet and electrically conductive. The flow of current between the comb patterns above a threshold value, in this invention chosen to be above 1 mA, will be the indication that the relative humidity in the data center has gone above 62%. Once the relative humidity goes below 62%, the salt will become dry and the current flow across the patterns will go below the threshold value. The leakage current time periods above and below the threshold value will be digitally logged in the data logger 245 at regular time intervals and available for down loading to a computer for display as a plot of high relative humidity events when the relative humidity went above 62% as a function of time.

The microcontroller can also control an air control unit 260 such as a humidifier, dehumidifier, air conditioner or air dampener to affect corresponding desired changes in the relative humidity levels in the air. An air mixer may be used to combine indoor and outdoor air to affect changes in the indoor relative humidity.

The technique can be used to monitor a rise above another relative humidity by choosing a salt with the appropriate deliquescent relative humidity. Each salt has a deliquescent relative humidity above which it absorbs enough moisture to get wet and therefore ionically conductive. For, example sodium nitrite has a deliquescent relative humidity of 62% at room temperature. If one wishes to monitor a rise above 75% relative humidity, a quartz frit containing sodium chloride salt particles may be used due to sodium chloride having a deliquescent relative humidity of 75%. Hence, a different salt solution may be used to test different relative humidity threshold levels. The salt solutions may be applied by various methods, such as either soaking the fritz disc or circuit to achieve maximum coverage or spraying the solution onto the comb patterns. Other methods of applying the solution may also be used.

Inter-digitated comb pattern may also be printed on other substrates besides the quartz frit disk such as on printed circuit boards that have been sand blasted to make the board surface rough enough to retain the salt particles bridging the combs. The pits on the printed circuit board between the combs may be loaded with salt particles by drying the saturated salt solution painted on the board surface. The inter-digitated comb pattern may be made of other metals besides platinum or gold.

Figure 3:
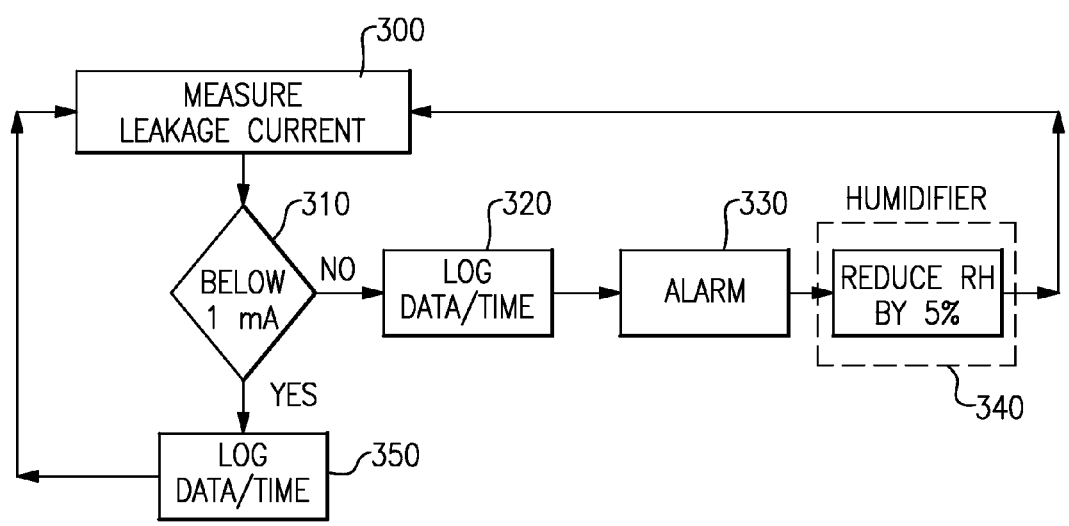
FIG. 3 depicts the process to check for relative humidity exceeding the preset threshold.

FIG. 3 demonstrates the relative humidity check process in a circuit implementing an embodiment. The circuit determines that relative humidity has exceeded the threshold level by measuring the leakage current 300. If leakage current is not below 1 mA in 310, data containing relevant information such as date, time, and duration of the threshold being exceeded is written to a data logger in 320. The alarm is triggered in 330. The circuit may be connected to an air control unit 340 which can adjust relative humidity levels. In this example, the air control unit is a humidifier, which is activated to reduce relative humidity by 5%. The process then returns to step 300 for continued monitoring.

If the leakage current remains below the preset threshold of 1 mA in step 310, then relevant information such as date, time, and duration of relative humidity remaining below the threshold is recorded to the data logger in 350. The process then returns to step 300 for continued monitoring.

Figure 4:
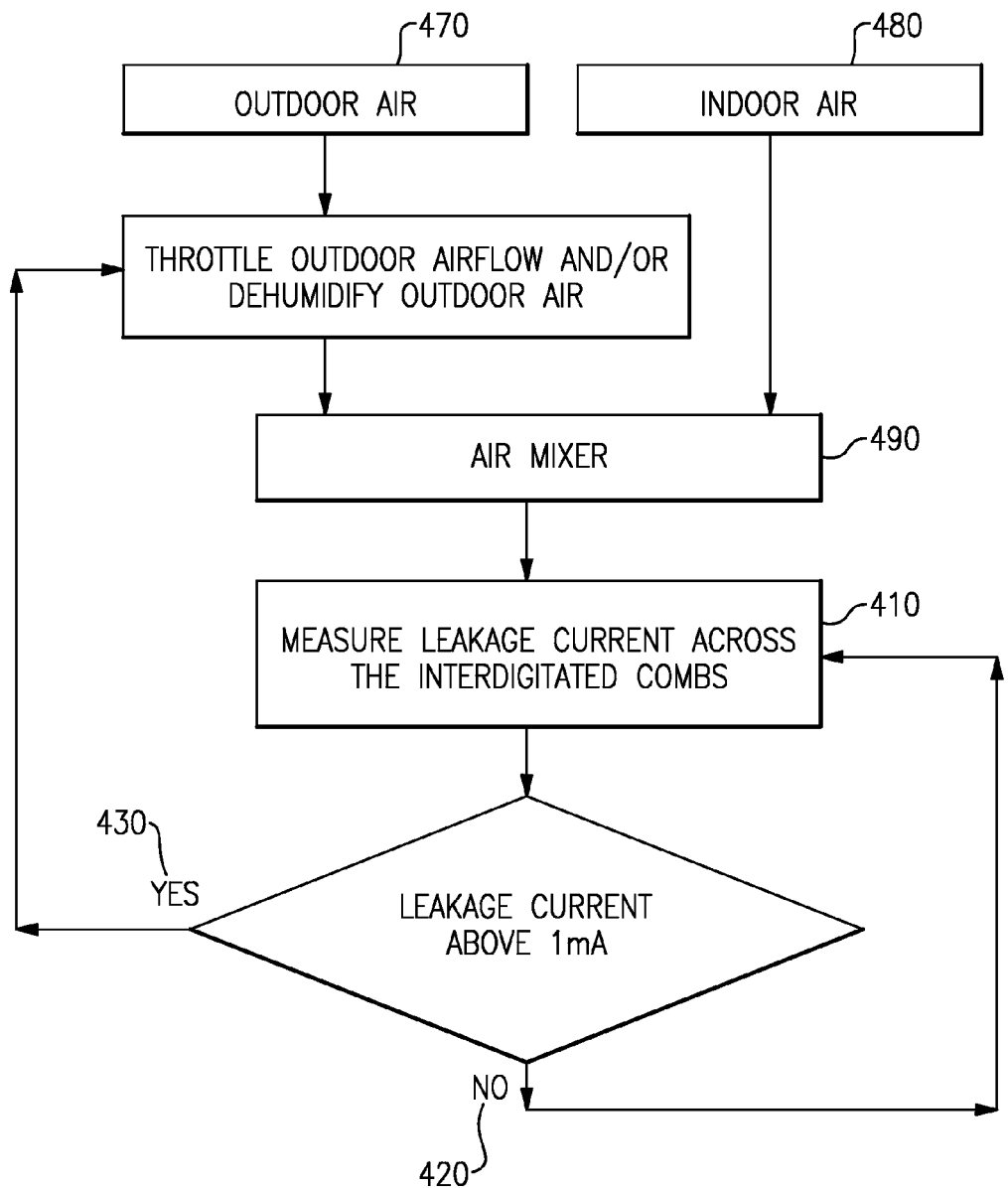
FIG. 4 depicts the process to check for relative humidity exceeding the preset threshold including use of an air mixer.

FIG. 4 demonstrates an embodiment involving an air mixer that combines indoor and outdoor air as another mechanism to control relative humidity levels inside the server room. The current through the inter-digitated combs is measured for leakage in 410. If current leakage does not exceed 1 mA, the process continues measuring for leakage in 420. If current leakage exceeds 1 mA this indicates a high relative humidity level 430 and action is taken to adjust the relative humidity level in the server room. Outdoor air 470 is mixed with indoor air 480 and combined with air mixer 490. Prior to reaching the air mixed, outdoor air may be conditioned by throttling the amount of air and/or dehumidifying the outdoor air to achieve desired relative humidity levels.

In another embodiment, relative humidity forecasting from national weather models may be used to make predictions concerning future relative humidity conditions, allowing proactive measures to be taken. Such measures may include closing air dampers, and/or adjusting temperature based on predicted changes in air and relative humidity levels. The sensors can then be used to monitor the effectiveness and accuracy of such measures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to explain the principles of the invention and the practical application, and to enable others of ordinary skill in the art to understand the invention through various embodiments and the various modifications thereto which are dependent on the particular use contemplated.

We claim:

1. A method to monitor the relative humidity of the air exceeding a predefined value, the method comprising:
    providing metallic inter-digitated comb patterns printed on a medium having spacing in between the patterns;
    coating the patterns and medium with a liquid solution containing salt, the salt having a deliquescent relative humidity;
    allowing the solution to dry;
    connecting a power supply, a resistor and a microprocessor to the comb pattern thereby creating an electrical circuit;
    connecting at least one of a data logger and an alarm circuit to the microprocessor;
    monitoring, by the microprocessor, the resistance of the circuit as voltage passes through the circuit;
    writing data to the data logger at regular time intervals and when the relative humidity of the air exceeds the predefined value, wherein the digitally logged data is available for downloading to a computer for display as a plot of high relative humidity, wherein the digitally logged data comprises date, time, and the duration of the predefined value being exceeded; and
    triggering the alarm circuit in response to the voltage exceeding a threshold value.

2. The method of claim 1 wherein the medium is a printed quartz frit disk.

3. The method of claim 1 further comprising activating an air mixer controlled by the microprocessor to combine indoor and outdoor air to regulate relative humidity levels of the indoor air based on received relative humidity forecasting from national weather models, wherein the microprocessor is designed to predict future humidity levels based on the received relative humidity forecasting.

4. The method of claim 1 further comprising activating an air control unit controlled by the microprocessor to regulate relative humidity levels of the indoor air, wherein the microprocessor is designed to instruct the air control unit to close air dampers and adjust temperature based on the relative humidity of the air exceeding the predefined value.

5. The method of claim 1 wherein the comb patterns are made of corrosion resistant metal.

* * * * *